United States Patent [19]
Lee, Jr. et al.

[11] Patent Number: 6,109,486
[45] Date of Patent: Aug. 29, 2000

[54] DRY SAND PLUVIATION DEVICE

[75] Inventors: Landris Thomas Lee, Jr.; Levi Rodgers Coffing, Jr., both of Vicksburg, Miss.

[73] Assignee: U.S. Army Corps of Engineers as represented by the Secretary of the Army, Washington, D.C.

[21] Appl. No.: 09/270,797

[22] Filed: Mar. 17, 1999

[51] Int. Cl.[7] ....................................... B65B 1/00
[52] U.S. Cl. ............... 222/485; 222/181.2; 222/480; 222/482
[58] Field of Search ................ 222/181.2, 478, 222/480, 481, 482, 484–486

[56] References Cited

U.S. PATENT DOCUMENTS

| | | | |
|---|---|---|---|
| 3,314,575 | 4/1967 | Graham | 222/485 |
| 4,175,680 | 11/1979 | Sammut | 222/486 |
| 4,342,407 | 8/1982 | Citrin | 222/485 |
| 5,273,188 | 12/1993 | Sanino | 222/482 |
| 5,493,852 | 2/1996 | Stewart | 222/485 |
| 5,598,953 | 2/1997 | Magargle et al. | 222/181.2 |

*Primary Examiner*—J. Casimer Jacyna
*Attorney, Agent, or Firm*—Luther A. Marsh

[57] ABSTRACT

Dry sand is "rained" or pluviated into a receptor container used in the study of soil mechanics. A supply vessel in the shape of an open-top rectangular box has four vertical side walls, a perforated bottom tray, and a slidable perforated tray in contact therewith, whereby sand flows by gravity from the supply vessel through perforations in the stationary and slidable trays and "rains" or pluviates into the receptor container when the slidable tray is in the "open" position, and sand is blocked from flowing from the supply vessel with the slidable tray in the "closed" position.

1 Claim, 2 Drawing Sheets

Section B - B'

DRY SAND PLUVIATION DEVICE

GOVERNMENT INTEREST STATEMENT

The invention described herein may be manufactured, licensed, and used by or for governmental purposes without the payment of any royalties thereon.

BACKGROUND OF THE INVENTION

This invention relates to a device used in the study of soil mechanics by means of physically modeling soil behavior. Specifically, it relates to a device for uniformly distributing fine dry sand particles in a receptor container to achieve uniform layering with consistent soil density properties. This invention also relates to a process for uniformly distributing fine sand into the receptor container. The receptor container is then spun in a centrifuge in order to simulate the compressive stress of overlying soil or fluids. During centrifuge flight, the receptor is shaken in a controlled manner to simulate a dynamic event such as an earthquake. Observing the soil behavior before, during, and after the dynamic event allows comparisons to be made between physical and numerical models. Typically, the physical model behavior is observed for numerical model verification and validation.

In the study of soil mechanics under simulated field conditions, when a small-scale soil model is constructed, it is critical that the soil particles be placed in a uniform fashion allowing a precisely controlled and consistent soil layer density. With current practice, in which soil particles are dumped into a receptor container through a single bottom outlet hose on a supply hopper, soil particles are not uniformly distributed; consequently, soil model tests may yield misleading and inaccurate results.

SUMMARY OF THE INVENTION

The object of this invention is to overcome the disadvantages of uneven, non-uniform soil particle placement in a receptor container used for soil mechanics studies. The process of uniformly distributing soil particles, specifically sand, in a receptor container is referred to "pluviation," a term related to the Latin word for "rain" and referring to the fact that the sand particles fall like raindrops.

The pluviation device of this invention is a supply vessel for soil particles, typically dry sand passing a 30 mesh screen but retained on a 200 mesh screen, for "raining" such soil particles by gravity into a receptor container, which is not part of this invention. The receptor container is subsequently spun in a centrifuge, which simulates the compressive stress under field condition which is due to the weight of overlying soil or fluids.

The vessel of this invention is an open-top rectangular box having four vertical side walls and a horizontal bottom tray with multiple perforations, preferably circular in shape and uniformly spaced on a square or equilateral triangular pattern. The vessel furthermore has a movable, slidable tray disposed below the stationary bottom tray of the vessel and in contact therewith. This slidable tray has corresponding multiple perforations matching those in the stationary tray in spacing and orientation. The stationary tray is referred to herein as the upper tray and the slidable tray as the lower tray.

When the perforations in the upper and lower trays are aligned, soil particles such as sand flow from the supply vessel to the receptor container. This is referred to as the "open" position. When the lower tray is slid sideways, the perforations in the upper tray are blocked by the lower tray and no flow of sand particles takes place. This is referred to as the "closed" position.

This invention also relates to a process for uniformly distributing fine sand into the receptor container with the vessel of this invention.

DETAILED DESCRIPTION OF THE INVENTION

Figure 1:
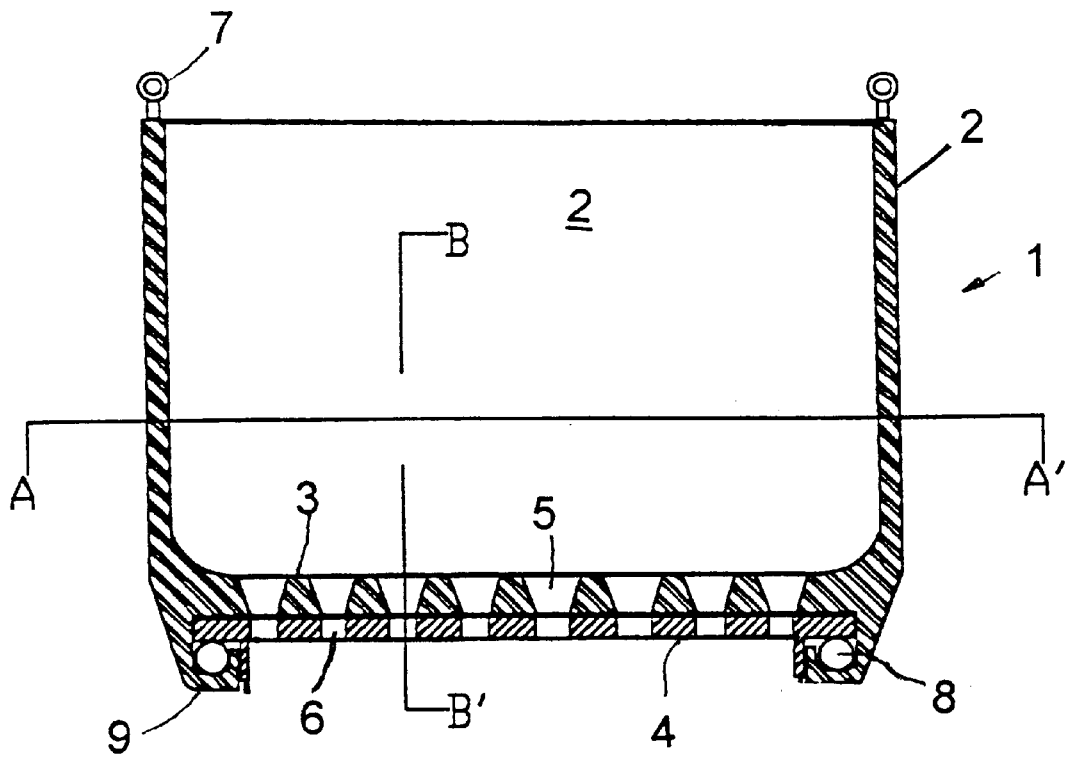
FIG. 1 is an elevational section of the supply vessel.

With reference to FIG. 1, a supply vessel 1 for soil particles such as sand is used in the study of soil mechanics, wherein sand is pluviated into a receptor container (not illustrated) disposed below the supply vessel. The supply vessel 1 is an open-top rectangular box comprising four vertical vessel side walls 2 and a horizontal stationary tray 3 forming the bottom of the vessel and having multiple regularly-spaced perforations 5, preferably circular in shape. The stationary tray 3 is herein referred to as the upper tray.

Figure 2:
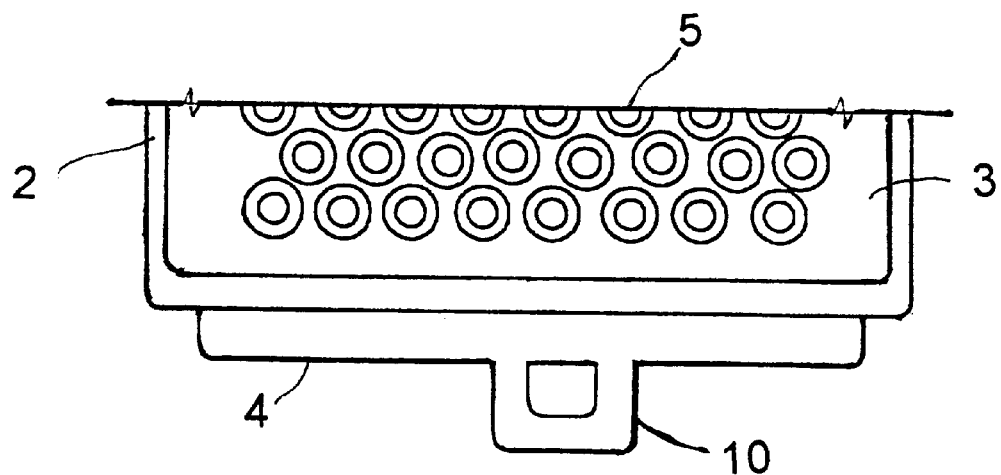
FIG. 2 is a plan view of a portion of the supply vessel as seen from A—A'.
Figure 3:
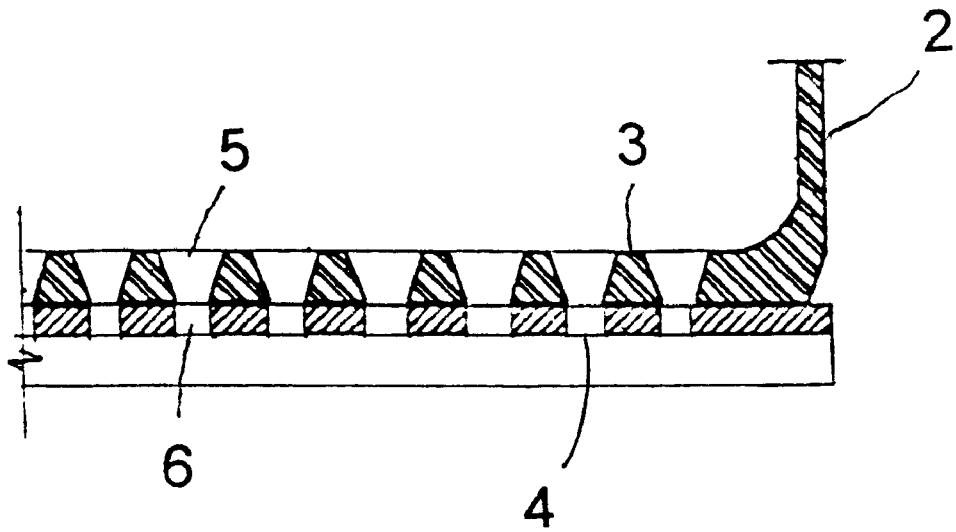
FIG. 3 is a partial elevational section along line B—B' with the perforations in the upper and lower trays in alignment, in the "open" position.
Figure 4:
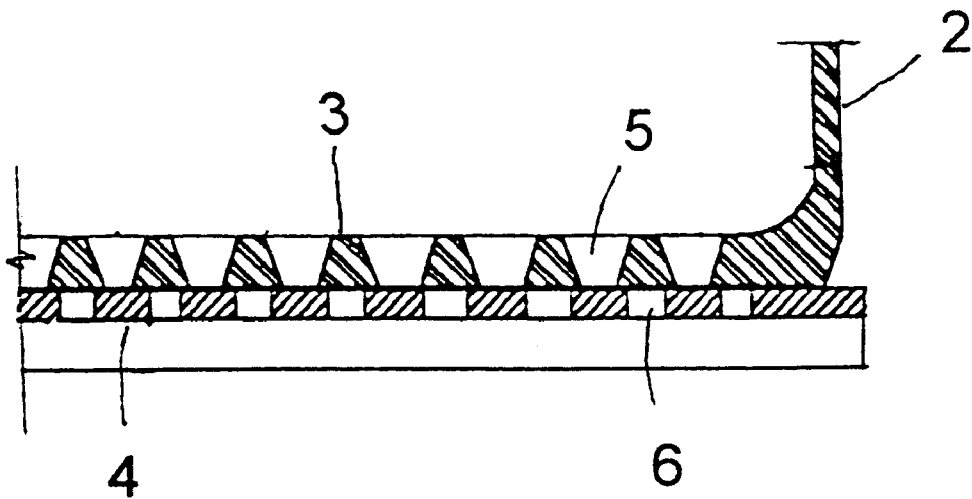
FIG. 4 is a partial elevational section along line B—B' with the perforations blocked, in the "closed" position.

A horizontal slidable tray 4, herein referred to as the lower tray, is disposed below the upper, stationary tray 3 and in sliding contact therewith. As seen in FIG. 2, the stationary tray 3 has multiple regularly-spaced perforations 5. As seen in FIGS. 3 and 4, the lower, slidable tray 4 has multiple perforations 6 matching the perforations in the upper tray in terms of spacing and orientation. In the "open" position of the lower tray 4, the perforations in the upper and lower trays, 5 and 6, respectively, are in alignment, and in the "closed" position of the lower tray 4, the perforations 5 of the upper tray are blocked by the lower tray 3. FIGS. 3 and 4 illustrate the "open" and "closed" positions of the lower tray 4, respectively.

The perforations in both the upper and lower tray, 5 and 6, may be cylindrical. Preferably, however, the perforations 5 in the upper tray are conical, or beveled, with the diameter of the perforation at the upper end larger than the diameter at the lower end thereof. This feature facilitates the flow of sand during the pluviation process. The conical angle of the perforations 5 in the upper tray may range from about 20 to about 60 degrees.

The perforations 5 and 6 in the upper and lower trays. 3 and 4, may be disposed on an equilateral triangular pattern, as shown in FIG. 2, or on a square pattern (not illustrated). Perforation diameters may range from 2 to 10 mm, and perforation spacing, center-to-center, may range from about 10 mm to about 30 mm.

The vessel 1 further comprises means 7 at the top edge of the side walls 2 for attachment to a hoist (not shown). This makes it possible to raise and lower the supply vessel land thereby to control and to adjust the height of the drop of sand particles during the pluviation process. Eye hooks may be used as means for attachment to a hoist.

The lower tray 4 is movably supported along two opposing edges by recessed tracks 9 containing multiple ball bearings 8 upon which the lower tray rests and which enable it to slide back and forth freely. The tracks 9 are affixed at the interior sides of the lower edges of two opposing sidewalls 2. Alternatively, roller bearings in recessed tracks or support brackets may be used (not illustrated). The horizontal movement of the lower tray 4 may be limited by stops or shoulders (not illustrated). A handle 10 attached to the lower tray 4 may be provided to facilitate manual positioning of the lower tray 4.

When the lower tray 4 is in the "open" position, sand flows by gravity from the supply vessel 1 through the perforations 5 and 6 in the upper and lower trays, 3 and 4, and "rains" or pluviates into the receptor container. FIG. 3 illustrates the "open" position. When the lower tray 4 is in the "closed" position, sand is blocked from flowing from the supply vessel 1 into the receptor container. FIG. 4 illustrates the "closed" position.

The pluviation process comprises filling the supply vessel with dry sand with the lower slidable tray in the "closed" position, leveling the surface of the sand, positioning the supply vessel above the receptor vessel at a predetermined height, sliding the lower tray into the "open" position, allowing the sand to pluviate or "rain" into the receptor vessel, and sliding the lower tray into the "closed" position, thereby stopping the pluviation of sand, when an appropriate sand level in the receptor container has been reached.

Although this invention has been described with regard to exemplary embodiments thereof, it will be understood by those skilled in the art that variations and modifications can be effected in this exemplary embodiment without departing from the scope and spirit of the invention.

What is claimed is:

1. A process for pluviating dry sand into a receptor vessel from a supply vessel, said receptor vessel comprising (a) four vertical vessel side walls; (b) a horizontal, stationary upper tray forming the bottom of the vessel and having multiple regularly-spaced perforations; (c) a horizontal, slidable lower tray disposed below the stationary tray and in sliding contact therewith, having corresponding multiple regularly-spaced perforations; and (d) means affixed at the interior sides of the lower edges of two opposing sidewalls for movably supporting the lower tray: wherein the multiple regularly-spaced perforations in the upper and lower trays have identical spacing and orientation, and wherein, in the "open" position of the lower tray, the perforations of the upper and lower trays are in alignment, and in the "closed" position of the lower, the perforations of the upper tray are blocked by the lower tray comprising dispensing the sand into the receptor vessel when the lower tray is in the "open" position, and stopping the flow of sand into the receptor vessel by moving the lower tray into the "closed" position.

* * * * *